United States Patent [19]
Chan et al.

[11] Patent Number: 5,804,166
[45] Date of Patent: Sep. 8, 1998

[54] LOW VOC HAIR SPRAYS CONTAINING CELLULOSE ETHERS

[75] Inventors: Anita N. Chan; Anthony B. Clayton, both of Wilmington; Jashawant J. Modi, Hockessin, all of Del.

[73] Assignee: Hercules Incorporated, Wilmington, Del.

[21] Appl. No.: 854,049

[22] Filed: May 9, 1997

[51] Int. Cl.[6] ..................................... A61K 7/00
[52] U.S. Cl. .................. 424/47; 424/401; 536/84; 536/90; 536/91; 536/95; 536/96; 536/97; 536/98; 536/99; 536/100; 536/101
[58] Field of Search ............. 424/47, 401; 536/84, 536/90, 91, 95, 96, 97, 98, 99, 100, 101

[56] References Cited

U.S. PATENT DOCUMENTS

| | | | |
|---|---|---|---|
| 3,210,251 | 10/1965 | Klug | 167/87 |
| 3,715,428 | 2/1973 | Quasius et al. | 424/47 |
| 3,741,783 | 6/1973 | Tunc | 106/189 |
| 4,228,277 | 10/1980 | Landoll | 536/90 |
| 4,243,802 | 1/1981 | Landoll | 536/91 |
| 4,803,071 | 2/1989 | Iovine et al. | 424/70 |
| 4,939,192 | 7/1990 | t'Sas | 524/44 |
| 5,068,099 | 11/1991 | Sramek | 424/47 |
| 5,104,646 | 4/1992 | Bolich, Jr. et al. | 424/70 |
| 5,106,609 | 4/1992 | Bolich, Jr. et al. | 424/70 |
| 5,126,124 | 6/1992 | Tazi et al. | 424/47 |
| 5,160,729 | 11/1992 | Login et al. | 424/47 |
| 5,176,898 | 1/1993 | Goldberg et al. | 424/47 |
| 5,182,098 | 1/1993 | Kopolow et al. | 424/47 |
| 5,206,009 | 4/1993 | Watling et al. | 424/45 |
| 5,221,531 | 6/1993 | Kopolow et al. | 424/71 |
| 5,294,437 | 3/1994 | Shah et al. | 424/71 |
| 5,326,555 | 7/1994 | Hardy et al. | 424/71 |
| 5,435,993 | 7/1995 | Hamilton et al. | 424/47 |
| 5,480,984 | 1/1996 | Angerer et al. | 536/88 |
| 5,512,276 | 4/1996 | Lang et al. | 424/70.11 |

OTHER PUBLICATIONS

Hercules Incorporated, *Research Disclosure*, 252002 (Apr. 10, 1985), "Use of Hydrophobically Modified Hydroxyethyl Cellulose which Adheres or is Substantive to Human Hair and Imparts Manageability to it."

Hercules Incorporated, *Research Disclosure*, 261025 (Jan. 10, 1986), "Hair Curl Retention Aid Comprises Amino–Ethylated or Cationic Hydroxypropyl Cellulose."

*Primary Examiner*—Nathan M. Nutter
*Attorney, Agent, or Firm*—Martin F. Sloan

[57] ABSTRACT

Disclosed are hair spray compositions containing non-ionic cellulosic ethers in a solvent base containing water and volatile organic solvent wherein the level of volatile organic solvent in the composition is about 80% or less, and wherein the non-ionic cellulose ether is characterized by a solution viscosity of less than about 50 cps at 25° C. for an aqueous solution containing 3 wt. % solids and 55 wt. % ethanol. The preferred non-ionic cellulosic ether is methylhydroxypropyl cellulose.

47 Claims, No Drawings

LOW VOC HAIR SPRAYS CONTAINING CELLULOSE ETHERS

FIELD OF THE INVENTION

This invention relates to aerosol hair spray compositions.

BACKGROUND OF THE INVENTION

The two major types of hair sprays commercially available are pump hair sprays and aerosol hair sprays. Both generally contain solvents, polymeric resin, and in some cases surfactants and fragrances. The resin is the ingredient primarily responsible for the curl retention properties that are characteristic of hair sprays.

The predominant solvent in both hair spray types is alcohol. However, for environmental reasons, legislation has been enacted in several states that restricts the amount of volatile organic compound (VOC) in aerosol products to 55% of the total solvent base. As the VOC's are removed from hair spray formulations to reach the 55% level, they are being replaced with water for economic and environmental reasons.

For new hair spray formulations containing high levels of water there is a need for polymeric resins that are soluble in the highly aqueous solvent base and which provide the proper combination of fast drying time and curl retention.

U.S. Pat. Nos. 5,176,898; 5,326,555; 5,206,009; 5,126,124 and 5,182,098 disclose aqueous hair spray compositions having VOC contents less than 80% and containing polymeric resins comprising a variety of vinyl copolymers.

U.S. Pat. No. 3,210,251 teaches the use of hydroxypropyl cellulose in a hair spray based on absolute alcohol solvent base.

U.S. Pat. No. 4,803,071 discloses aerosol propelled hair fixatives containing a water-soluble cationic graft copolymer prepared by polymerizing N,N'-dialkyldiallyl ammonium halide monomer with substrate selected from the group consisting of hydroxyethyl cellulose and hydroxypropyl cellulose.

In U.S. Pat. No. 3,741,783 there is disclosed hair spray containing sulfated alkali cellulose ether in a base containing at least 60% alcohol.

U.S. Pat. 3,715,428 relates to hair spray compositions containing polymeric quaternary cellulose ether salts in an aqueous alcohol solvent base containing from 20 to 80% water.

U.S. Pat. Nos. 5,104,646 and 5,106,609 disclose cosmetic compositions containing a two-component thickening system comprising a) a hydrophobically modified nonionic cellulose ether having a sufficient degree of nonionic substitution to cause it to be water-soluble and being further substituted with a long chain alkyl radical in an amount which renders the cellulose ether less than 1% by weight soluble in water, and b) water-soluble surfactant, in a solvent base of water or water lower alkanol mixture. The use of the compositions as hair care products and shampoos is disclosed.

SUMMARY OF THE INVENTION

A hair spray composition comprises at least one water-soluble, non-ionic cellulose ether dissolved in a base comprising water and volatile organic solvent, wherein the level of the volatile organic solvent in the composition is about 80% by weight or less, and wherein the non-ionic cellulose ether is characterized by a solution viscosity of less than about 50 cps. at 25° C. for an aqueous solution containing 3 wt. % solids, 55 wt. % ethanol and 42 wt. % water.

A method for styling hair comprises spraying the hair with an effective amount of the hair spray composition of the invention.

DETAILED DESCRIPTION OF THE INVENTION

The term "water-soluble" as used herein means at least about 1% solubility in water at ambient temperature.

The water-soluble non-ionic cellulose ethers for use in the invention include hydroxyethyl cellulose (HEC), hydroxypropyl cellulose (HPC), water soluble ethylhydroxyethyl cellulose (EHEC), hydroxypropylhydroxyethyl cellulose (HPHEC), methyl cellulose (MC), methylhydroxypropyl cellulose (MHPC), methylhydroxyethyl cellulose (MHEC), hydrophobically modified hydroxyethyl cellulose (HMHEC), hydrophobically modified hydroxypropyl cellulose (HMHPC), hydrophobically modified ethylhydroxyethyl cellulose (HMEHEC), hydrophobically modified hydroxypropylhydroxyethyl cellulose (HMHPHEC), hydrophobically modified methyl cellulose (HMMC), hydrophobically modified methylhydroxypropyl cellulose (HMMHPC), hydrophobically modified methylhydroxyethyl cellulose (HMMHEC), and mixtures thereof. The preferred water-soluble non-ionic cellulose ethers are methylhydroxypropyl cellulose and hydrophobically modified hydroxyethyl cellulose. The most preferred is methylhydroxypropyl cellulose, also known in the art as hydroxypropylmethyl cellulose.

Methods for producing hydrophobically modified hydroxyethyl cellulose by reacting hydroxyethyl cellulose with alkylglycidyl ethers where the alkyl group contains from 1 to 10 carbon atoms are disclosed by t'Sas in U.S. Pat. No. 4,939,192, which is incorporated herein in its entirety by reference. Methods for producing hydrophobically modified hydroxyethyl cellulose by substituting hydroxyethyl cellulose with hydrocarbon radicals having from about 10 to 24 carbon atoms are disclosed in U.S. Pat. No. 4,228,277 to Landoll, which is incorporated herein in its entirety by reference. In this patent, a variety of chemical methods for attaching the hydrocarbon radicals is disclosed. For the instant invention, etherification of hydroxyethyl cellulose with moieties containing about 4 to about 24 carbon atoms in an amount of from about 0.05 to about 3 wt. % is preferred. The most preferred hydrophobically modified hydroxyethyl cellulose is substituted by a radical containing about 16 carbon atoms in an amount of from about 0.05 to about 3 wt. %.

For satisfactory spraying performance, it is preferred that the hair spray compositions have viscosities less than about 50 cps at ambient temperature, i.e., about 25° C. More preferably the viscosity is from about 5 to about 50 cps, and most preferably from about 5 to about 25 cps at 25° C.

The non-ionic cellulose ethers which perform satisfactorily in the instant invention are characterized by a solution viscosity of less than about 50 cps at 25° C. for an aqueous solution containing 3 wt. % solids and 55 wt. % ethanol, i.e., a solution containing 3 parts of cellulose ether, 55 parts of ethanol and 42 parts of water. In order to achieve viscosities in the desired range it is preferred that the weight average molecular weight ($M_w$) of the non-ionic cellulose ether be less than about 150,000. More preferably the weight average molecular weight is less than about 75,000, even more preferably less than about 50,000, and most preferably from about 25,000 to about 50,000.

A chemical method for preparing low molecular weight, low viscosity polysaccharides and polysaccharide derivatives by treatment of them with hydrogen peroxide is disclosed in U.S. Pat. No. 5,480,984, which is incorporated herein by reference in its entirety.

The preferred level of non-ionic cellulose ether in the hair spray compositions is about 1 wt. % or greater. More preferably the level is about 1 wt. % to about 10 wt. %, even more preferably about 2 wt. % to about 7 wt. %, and most preferably about 3 wt. % to about 5 wt. %.

The hair spray compositions of this invention are solutions containing non-ionic cellulose ether in a blend of water and one or more water-miscible volatile organic compounds (VOC). The composition will contain 80% or less by weight volatile organic solvent. Preferably it will contains 65% or less, and most preferably 55% or less by weight volatile organic solvent. Typically the volatile organic solvent will be a low boiling alcohol, acetal or ketone, such as methanol, ethanol, n-propanol, i-propanol, butanol, acetone or dimethoxymethane. For use in the instant invention, alcohols, most preferably ethanol, are preferred.

In addition to the non-ionic cellulose ethers the hair spray compositions of this invention may contain other polymers well known in the art to be used in hair sprays. These include polyvinylpyrrolidone, vinylpyrrolidone/vinyl acetate copolymers, vinyl methyl ether/maleic anhydride copolymers, vinylpyrrolidone/acrylate copolymers, vinylpyrrolidone/dimethylaminoethylmethacrylate copolymers, vinylpyrrolidone/vinyl acetate/vinyl propionate copolymers, vinylpyrrolidone/vinyl caprolactam/dimethylaminoethylmethacrylate copolymers, vinyl acetate/crotonic acid copolymers, vinyl acetate/crotonic acid/vinyl propionate copolymers, vinyl acetate/crotonic acid/vinyl neodecanoate copolymers, acrylate/acrylamide copolymers, octylacrylamide/acrylate copolymers, octylacrylamide/acrylate/butylaminoethyl methacrylate copolymers, t-butyl acrylate/methacrylic acid/ethyl acrylate copolymers and water dispersible sulfonated polyester.

The hair spray compositions of this invention may further comprise aerosol propellant. The term "propellant" as used herein means compositions used to effect propellant action in aerosol systems. Suitable propellants include n-butane, isobutane, dimethyl ether, difluoroethane, chlorodifluoromethane, other chlorofluorocarbons, or mixtures thereof. Preferred propellants are dimethyl ether, 1,1-difluoroethane, n-butane, isobutane, or mixtures thereof. These propellants are manufactured by DuPont and are available under the trade names Dymel A, Dymel 152, Hydrocarbon A17 and Hydrocarbon A31. Preferably the amount of propellant used in the compositions ranges from about 10–40% based on the total weight of the composition.

It may also be desirable to incorporate other ingredients into the hair spray compositions of this invention. These include common additives such as anionic, cationic, amphoteric or nonionic wetting agents and emulsifiers, e.g. $C_{12}$- to $C_{18}$-alkyl ether sulfates, alkyltrimethylammonium salts, alkylpyridinium salts, carboxyl derivatives of imidazole, N-alkylsulfobetaine or polyglyceryl ether of saturated or unsaturated fatty alcohol and alkylphenols in amount of approximately 0.01 to 3% by weight; preservatives, e.g., salicylic acid or mandelic acid in quantities of about 0.01 to 0.7% by weight; anti-dandruff ingredients such as zinc pyridinethion; cosmetic dyes; hair grooming ingredients such as fatty acid esters, fatty alcohols, fatty acid glycerides, lanolin derivatives or pantothenic acid in amounts of about 0.01 to 3% by weight; waterproofing agents such as silicone oils; emollients such as phthalic acid esters or alkyl citrates; agents for facilitating combing such as cetyltrimethylammonium chloride, or polymers such as cationic chitosan derivatives, cellulose derivatives and guar derivatives in quantities of about 0.01 to 0.2% by weight; as well as complexing agents, foam stabilizers, buffers, light stabilizers, antioxidants, perfume oils and sun-screen agents in amounts of about 0.01 to 0.8% by weight.

The compositions of this invention are capable of being sprayed, exhibit rapid drying times when sprayed, and provide excellent holding power to hair, with minimal droop or tackiness under high humidity conditions. The holding power to hair of the compositions of this invention has been evaluated by measuring the Initial Curl Retention of hair tresses sprayed with the compositions and the Curl Retention after storage of the treated tresses at 90% relative humidity for up to 6 hours, hereinafter referred to as "High Humidity Curl Retention". Preferably these compositions impart to human hair an Initial Curl Retention and High Humidity Curl Retention of greater than about 15%, more preferably greater than about 45%, and most preferably greater than about 75%.

The drying times observed with the hair sprays of this invention, from about 23 to 25 minutes, are comparable to those observed with hair sprays similarly formulated with polymers widely used in the industry.

This invention is illustrated by the following examples, which are exemplary only and not intended to be limiting. All percentages, parts, etc., are by weight, unless otherwise indicated.

Evaluation Methods

Hair Spray Application

The spray pump utilized was a Seaquist Dispensing "Euromist", 160 mcl output, 24-410, with a 0.060 inch (inner diameter) dip tube with a 0.016×0.010 inch insert.

Target distance from the pump nozzle to the center of the curled tress was 6 inches.

Drying Time

A Sartorius Moisture Analyzer model MA30 was modified by addition of a switch to disable the heater. Samples for testing were applied to 4 inch diameter aluminum weighing pans.

For a test, the pan was weighed and mounted vertically on the test stand at a distance of about 6 inches from the spray bottle. Two or three strokes of the spray pump were carried out to provide a sample with a weight of approximately 0.240 g. The pan was immediately returned to the balance, and the lid was closed, automatically beginning the drying test. The output of the moisture analyzer was coupled to a computer such that drying rate curves were generated. The instrument was run in a fixed time mode, and the drying curve end point could be determined by observation. With the time span fixed at 30 minutes, for most of the formulations the weight stabilized at about 5–10% of the initial sample weight. Three or more samples of each formulation were tested. The result reported is the time to reach 10% of the original weight.

Initial Curl Retention and High Humidity Curl Retention

The test samples used to determine Initial Curl Retention and High Humidity Curl Retention were 2.0–2.05 g tresses of 9 inch long European Caucasian medium brown virgin hair from DeMeo Brothers, Inc., New York, N.Y. The tresses were assembled by binding the root ends of a 2 g sample of hair with two plastic cable ties located approximately ⅜ and 1 inch from the root ends. An approximately 4 inch length of 30 lb. test monofilament was formed into a loop and inserted into the end of the tress before the cable ties were secured. The tresses were further secured by applying several drops of cyanoacrylate adhesive to the bound area of the tress.

In preparation for testing, each tress was dry-combed to remove unsecured hairs and then wetted with tap water. Three ml of a 10% solution of ammonium lauryl sulfate in deionized water was applied to the tress with a syringe, and the tress was thoroughly kneaded for about 30 seconds. The tress was rinsed in tap water, and then the washing and rinsing procedure was repeated. The washing procedure was followed by a 30 second rinse under running deionized water. Each tress was then trimmed to 7 inches below the lowest cable tie. The tress was wet-combed two or three times and then wound with an end paper onto a ⅝ inch diameter hair curler. Eight tresses were prepared for each formulation to be tested. The tresses were hung by their loops and allowed to dry overnight in a controlled atmosphere room at 23° C., 50% relative humidity.

In preparation for spraying, the eight dried, curled tresses were hung in a controlled atmosphere room at 23° C., 50% relative humidity on a test rack scaled in ¼ inch increments, and the scale reading at the lowest cable tie was noted. The curler end papers were removed and the initial curl length at the bottom of the tress was noted.

The hair tress and hair spray bottle containing the composition to be evaluated were mounted in a test stand designed to fix the target distance between the spray head and the tress at 6 inches. The tress was sprayed with three pump strokes on one side, then reversed and sprayed again with three strokes on the reverse side. The tress was then returned to the test rack, and the total length of the curl was noted at 2, 4, 6, 8 and 10 minutes to determine the Initial Curl Retention.

The test rack was then placed in an Espec Model LHU-112 Humidity Cabinet set at 26.7° C. and 90% relative humidity. Readings of total curl length were taken at intervals of 15 minutes, 30 minutes, 1, 2, 3, 4, 5 and 6 hours to determine High Humidity Curl Retention.

Immediately upon completion of the test, the curls were transferred to the controlled atmosphere room at 23° C., 50% relative humidity, and the hand feel as regards tackiness, stiffness and brittleness was subjectively rated.

Curl Retention (% CD), both "Initial" and "High Humidity", was calculated as:

$$\% CD = 100(L-L_t)/(L-L_o)$$

where L is the length of the fully extended tress (7 inches), $L_t$ is the length of the tress at the time of test, and $L_o$ is the initial length of the tress before spraying. The percent High Humidity Curl Retention data reported herein are after 6 hours in the humidity cabinet.

Data for the eight curls were calculated as above and the average of the results reported.

Viscosity

Viscosity was measured in a 25° C. water bath with a Brookfield Viscometer Model LVDV-I+ equipped with a "UL" adapter for low viscosity fluids. Readings were taken after 2 minutes rotation at 12 or 30 rpm. Measurements were made in duplicate.

Materials

Culminal®8MP5C methylhydroxypropyl cellulose, available from Hercules Incorporated, Wilmington, Del. Three different lots of Culminal 8MP5C had an average solution viscosity (3 wt. % solids, 55 wt. % ethanol and 42 wt. % water at 25° C.) of 35.2 cps (ranging from 31.6 to 37.9 cps) and an average $M_w$ of 56,667 (ranging from 47,300 to 61,700) as determined by gel permeation chromatography.

Pharmacoat®606 methylhydroxypropyl cellulose, available from Shin-Etsu Chemical Co., Tokyo, Japan. The solution viscosity (3 wt. % solids, 55 wt. % ethanol and 42 wt. % water at 25° C.) was 23.7 cps and the $M_w$ was 44,200.

Methocel®E5 methylhydroxypropyl cellulose, available from Dow Chemical Co., Midland, Mich. The solution viscosity (3 wt. % solids, 55 wt. % ethanol and 42 wt. % water at 25° C.) was 17.0 cps and the $M_w$ was 34,200.

Natrosol®250LR, hydroxyethyl cellulose, available from Hercules Incorporated, Wilmington, Del. The solution viscosity (3 wt. % solids, 55 wt. % ethanol and 42 wt. % water at 25° C.) was 50.3 cps and the $M_w$ was 143,900.

AQU D3382, hydrophobically modified hydroxyethyl cellulose, available from Hercules Incorporated, Wilmington, Del. The solution viscosity (3 wt. % solids, 55 wt. % ethanol and 42 wt. % water at 25° C.) was 23.1 cps and the $M_w$ was 44,700.

Amphomer®LV-71: Octylacrylamide/acrylate/butylaminoethyl methacrylate copolymer, available from National Starch and Chemical Co., Bridgewater, N.J.

AQ48 Ultra Polymer: Sulfonated polyester, available from Eastman Chemical Co., Kingsport, Tenn.

Luvimer Low VOC: Acrylic copolymer, available from BASF Corp., Mount Olive, N.J.

Luviskol VA 73W: Acrylic copolymer, available from BASF Corp., Mount Olive, N.J.

EXAMPLES 1–11 AND COMPARATIVE EXAMPLES A–E

Examples 1–11 describe the evaluation of hair spray compositions of this invention. Comparative Examples A–E describe formulations prepared in the same way but using commercially available polymers used in hair spray formulations.

Samples of each formulation to be tested were prepared by weighing water and alcohol into a jar and then adding the polymer or polymer solution while mixing with a magnetic stirrer. The jar was capped to prevent loss of volatiles, and stirring was continued until the polymer was dissolved. The appearance of the formulation was noted with regard to color, clarity, homogeneity, separation and sediment. Solution stability was noted at intervals by inspecting for separation or settling. All compositions were formulated using SD 40A ethanol such that the final composition had 55% by weight ethanol. The results are presented in Tables 1 and 2.

TABLE 1

Evaluation of Hair Spray Formulations

|  | Polymer | $M_w$ | Polymer Solids, % | Viscosity, cps | pH | Initial Curl Retent., % | High Humidity Curl Retent., % | Drying Time, minutes[1] |
|---|---|---|---|---|---|---|---|---|
| Example 1 | Culminal 8MP5C | 61,000 | 3 | 36.1 |  | 84 | 72 | 24 |
| Example 2 | Culminal 8MP5C | 61,700 | 3 | 37.9 | 8.3 | 83 | 78 | 23 |
| Example 3 | Culminal 8MP5C | 61,700 | 2.25 | 23.0 | 8.6 | 87 | 58 | 23 |
| Example 4 | Culminal 8MP5C | 47,300 | 3 | 31.6 |  | 85 | 69 | 25 |
| Example 5 | Methocel E5 | 34,200 | 3 | 17.0 | 8.5 | 84 | 75 | 23 |
| Example 6 | Pharmacoat 606 | 44,200 | 3 | 23.7 | 8.5 | 81 | 72 | 24 |
| Example 7 | Pharmacoat 606 | 44,200 | 3 | 25.0 | 4.0 | 79 | 72 | 25 |
| Example 8 | Pharmacoat 606 | 44,200 | 3 | 24.5 | 10.5 | 82 | 71 | 25 |
| Example 9 | Natrosol 250LR | 143,900 | 3 | 50.3 | 9.0 | 76 | 29 | 25 |
| Example 10 | AQU D3382 | 44,700 | 3 | 23.1 |  | 73 | 19 | — |
| Example 11 | Klucel ELF |  | 3 | 17.6 |  | 89 | 22 | — |

[1] Time in minutes to reach 10% of initial sample weight (0.22–0.24 g).

TABLE 2

Evaluation of Hair Spray Formulations Containing Commercial Polymers

|  | Polymer | Polymer Solids, % | Viscosity, cps | Initial Curl Retent., % | High Humidity Curl Retent., % | Drying Time, minutes[1] |
|---|---|---|---|---|---|---|
| Comparative Example A | Amphomer LV71 | 5 | 13.8 | 88 | 78 | 21 |
| Comparative Example B | Amphomer LV71 | 3 | 10.6 | 86 | 73 | 21 |
| Comparative Example C | AQ-48 Ultra Polymer | 5 | 3 | 97 | 34 | 28 |
| Comparative Example D | Luviskol VA73W | 5 | 4 | 62 | 27 | 26 |
| Comparative Example E | Luviskol Low VOC | 5 | 8 | 91 | 58 | 14 |

[1] Time in minutes to reach 10% of initial sample weight (0.22–0.24 g).

The data in the tables demonstrate that the hair spray formulations of the invention exhibited Initial Curl Retention and Drying Time quite similar to, and in a few cases better than, the formulations based on polymers sold for hair spray formulations (Comparative Examples A–E). With exception of Examples 9–11, the High Humidity Curl Retention data demonstrate performance as good as or better than that of the polymers of the comparative examples. The comparison of the data in Examples 1–8 with that of Examples 9–11 demonstrates the most preferred status of methylhydroxypropyl cellulose in the practice of the invention.

Examples 7 and 8 demonstrate the relative insensitivity of the results to the pH of the spray composition.

EXAMPLES 13–15

These examples describe the performance of hairs spray compositions based on methylhydroxypropyl cellulose where the level of VOC in the composition is varied from 55% to 0% by weight. The data are presented in Table 3.

TABLE 3

Evaluation of Methylhydroxypropyl Cellulose[2] in Hair Spray Formulations at Several VOC Levels

|  | % VOC[3] | Polymer Solids, % | Viscosity, cps | Initial Curl Retent., % | High Humidity Curl Retent, % | Drying Time, minutes[1] |
| --- | --- | --- | --- | --- | --- | --- |
| Example 12 | 55 | 3 | 24 | 81 | 72 | 24 |
| Example 13 | 40 | 3 | 30 | 74 | 55 | 26 |
| Example 14 | 20 | 3 | 24 | 66 | 56 | 32 |
| Example 15 | 0 | 3 | 12 | 64 | 46 | 50 |

[1]·Time in minutes to reach 10% of initial sample weight (0.22–0.24 g)
[2]·Pharmacoat 606
[3]·VOC is ethanol; remainder of the solvent is water.

The data in Table 3 demonstrate that as the VOC level is reduced below 55%, Initial Curl Retention and High Humidity Curl Retention gradually fall, and the Drying Time increases.

It is not intended that the examples presented here should be construed to limit the invention, but rather they are submitted to illustrate some of the specific embodiments of the invention. Various modifications and variations of the present invention can be made without departing from the scope of the appended claims.

What is claimed is:

1. A hair spray composition comprising at least one water-soluble, non-ionic cellulose ether dissolved in a base comprising water and volatile organic solvent, wherein the level of volatile organic solvent in the composition is about 80% by weight or less, and wherein the non-ionic cellulose ether is characterized by a solution viscosity less than about 50 cps. at 25° C. for an aqueous solution containing 3 wt. % solids, 55 wt. % ethanol and 42 wt. % water, and wherein the hair spray composition is characterized by a viscosity satisfactory for spraying performance.

2. The hair spray composition of claim 1 wherein the level of the volatile organic solvent in the composition is about 65% by weight or less.

3. The hair spray composition of claim 2 wherein the level of the volatile organic solvent in the composition is about 55% by weight or less.

4. The hair spray composition of claim 1 wherein the level of non-ionic cellulose ether in the composition is about 1% by weight or greater.

5. The hair spray composition of claim 4 wherein the viscosity of the composition is less than about 50 cps at 25° C.

6. The hair spray composition of claim 5 wherein the viscosity of the composition is from about 5 to about 50 cps at 25° C.

7. The hair spray composition of claim 5 wherein the viscosity of the composition is from about 5 to about 25 cps at 25° C.

8. The hair spray composition of claim 1 further comprising aerosol propellant.

9. The hair spray composition of claim 1 wherein the volatile organic solvent is a water-miscible alcohol selected from the group consisting of ethanol, n-propanol and i-propanol.

10. The hair spray composition of claim 1 wherein the volatile organic solvent is ethanol.

11. The hair spray composition of claim 1 which when applied to human hair imparts to it Initial Curl Retention of greater than about 15%.

12. The hair spray composition of claim 1 which when applied to human hair imparts to it Initial Curl Retention greater than about 45%.

13. The hair spray composition of claim 1 which when applied to human hair imparts to it Initial Curl Retention greater than about 75%.

14. The hair spray composition of claim 1 which when applied to human hair imparts to it High Humidity Curl Retention greater than about 15%.

15. The hair spray composition of claim 1 which when applied to human hair imparts to it High Humidity Curl Retention greater than about 45%.

16. The hair spray composition of claim 1 which when applied to human hair imparts to it High Humidity Curl Retention greater than about 75%.

17. The hair spray composition of claim 1 wherein the non-ionic cellulose ether is selected from the group consisting of hydroxyethyl cellulose (HEC), hydroxypropyl cellulose (HPC), water soluble ethylhydroxyethyl cellulose (EHEC), hydroxypropylhydroxyethyl cellulose (HPHEC), methyl cellulose (MC), methylhydroxypropyl cellulose (MHPC), methylhydroxyethyl cellulose (MHEC), hydrophobically modified hydroxyethyl cellulose (HMHEC), hydrophobically modified hydroxypropyl cellulose (HMHPC), hydrophobically modified ethylhydroxyethyl cellulose (HMEHEC), hydrophobically modified hydroxypropylhydroxyethyl cellulose (HMHPHEC), hydrophobically modified methyl cellulose (HMMC), hydrophobically modified methylhydroxypropyl cellulose (HMMHPC), hydrophobically modified methylhydroxyethyl cellulose (HMMHEC), and mixtures thereof.

18. The hair spray composition of claim 1 wherein the non-ionic cellulose ether is selected from the group consisting of methylhydroxypropyl cellulose and hydrophobically modified hydroxyethyl cellulose.

19. The hair spray composition of claim 1 wherein the non-ionic cellulose ether is methylhydroxypropyl cellulose.

20. The hair spray composition of claim 1 wherein the non-ionic cellulose ether is hydrophobically modified hydroxyethyl cellulose.

21. The hair spray composition of claim 1 wherein the non-ionic cellulose ether has a weight average molecular weight ($M_w$) of less than about 150,000.

22. The hair spray composition of claim 1 wherein the non-ionic cellulose ether has a weight average molecular weight ($M_w$) of less than about 75,000.

23. The hair spray composition of claim 1 wherein the non-ionic cellulose ether has a weight average molecular weight ($M_w$) of less than about 50,000.

24. The hair spray composition of claim 1 wherein the non-ionic cellulose ether has a weight average molecular weight ($M_w$) of about 25,000 to about 50,000.

25. The hair spray composition of claim 20 wherein the hydrophobically modified hydroxyethyl cellulose is hydroxyethyl cellulose substituted with a long chain alkyl radical having 4 to 24 carbon atoms in an amount of from about 0.05 to about 3 wt. %.

26. The hair spray composition of claim 25 wherein the long chain alkyl group is attached via an ether linkage.

27. The hair spray composition of claim 25 wherein the long chain alkyl group is an alkyl group containing 16 carbons.

28. The hair spray composition of claim 1 wherein the non-ionic cellulose ether is at a level of from about 1% to about 10 wt. % based on the total weight of the hair spray composition.

29. The hair spray composition of claim 28 wherein the non-ionic cellulose ether is at a level of from about 2 to about 7 wt. % based on the total weight of the hair spray composition.

30. The hair spray composition of claim 29 wherein the non-ionic cellulose ether is at a level of from about 3 to about 5 wt. % based on the total weight of the hair spray composition.

31. The hair spray composition of claim 1 wherein the volatile organic solvent is a water-miscible alcohol selected from the group consisting of ethanol, n-propanol and i-propanol, and the non-ionic cellulose ether is selected from the group consisting of methylhydroxypropyl cellulose and hydrophobically modified hydroxyethyl cellulose.

32. The hair spray composition of claim 1 wherein the volatile organic solvent is ethanol, and the non-ionic cellulose ether is methylhydroxypropyl cellulose having a weight average molecular weight ($M_w$) less than about 150,000.

33. The hair spray composition of claim 1 wherein the volatile organic solvent is ethanol, and the non-ionic cellulose ether is hydrophobically modified hydroxyethyl cellulose having a weight average molecular weight ($M_w$) less than about 150,000, wherein the hydrophobically modified hydroxyethyl cellulose is hydroxyethyl cellulose substituted with a long chain alkyl radical having 4 to 24 carbon atoms in an amount of from about 0.05 to about 3 wt. %.

34. The hair spray composition of claim 32 wherein the methylhydroxypropyl cellulose is a level of from about 1% to about 10 wt. % based on the total weight of the hair spray composition, and the viscosity of the hair spray composition is from about 5 to about 50 cps at 25° C.

35. The hair spray composition of claim 33 wherein the hydrophobically modified hydroxyethyl cellulose is at a level of from about 1% to about 10 wt. % based on the total weight of the hair spray composition, and the viscosity of the hair spray composition is from about 5 to about 50 cps at 25° C.

36. The hair spray composition of claim 34 which when applied to human hair imparts to it Initial Curl Retention and High Humidity Curl Retention greater than about 15%.

37. The hair spray composition of claim 35 which when applied to human hair imparts to it Initial Curl Retention and High Humidity Curl Retention greater than about 15%.

38. A method for styling hair comprising:

a) spraying the hair with an effective amount of the hair spray composition of claim 1; and b) allowing the hair to dry.

39. The method of claim 38 wherein the level of the volatile organic solvent in the hair spray composition is about 65% by weight or less.

40. The method of claim 38 wherein the level of the volatile organic solvent in the hair spray composition is about 55% by weight or less.

41. The method of claim 38 wherein the level of non-ionic cellulose ether in the hair spray composition is about 1% by weight or greater.

42. The method of claim 38 wherein the viscosity of the hair spray composition is less than about 50 cps at 25° C.

43. The method of claim 38 wherein the non-ionic cellulose ether is selected from the group consisting of hydroxyethyl cellulose (HEC), hydroxypropyl cellulose (HPC), water soluble ethylhydroxyethyl cellulose (EHEC), hydroxypropylhydroxyethyl cellulose (HPHEC), methyl cellulose (MC), methylhydroxypropyl cellulose (MHPC), methylhydroxyethyl cellulose (MHEC), hydrophobically modified hydroxyethyl cellulose (HMHEC), hydrophobically modified hydroxypropyl cellulose (HMHPC), hydrophobically modified ethylhydroxyethyl cellulose (HMEHEC), hydrophobically modified hydroxypropylhydroxyethyl cellulose (HMHPHEC), hydrophobically modified methyl cellulose (HMMC), hydrophobically modified methylhydroxypropyl cellulose (HMMHPC), hydrophobically modified methylhydroxyethyl cellulose (HMMHEC), and mixtures thereof.

44. The method of claim 38 wherein the non-ionic cellulose ether is methylhydroxypropyl cellulose.

45. The method of claim 38 wherein the non-ionic cellulose ether is hydrophobically modified hydroxyethyl cellulose.

46. The method of claim 38 wherein the hydrophobically modified hydroxyethyl cellulose is hydroxyethyl cellulose substituted with a long chain alkyl radical having 4 to 24 carbon atoms in an amount of from about 0.05 to about 3 wt. %.

47. The method of claim 38 wherein the non-ionic cellulose ether is at a level of from about 1% to about 10 wt. % based on the total weight of the hair spray composition.

* * * * *